US012558444B2

(12) United States Patent
Forhan

(10) Patent No.: US 12,558,444 B2
(45) Date of Patent: Feb. 24, 2026

(54) ELECTRONIC SANITIZING DEVICES AND METHODS

(71) Applicant: Eypex Corporation, Pontiac, MI (US)

(72) Inventor: Peter Forhan, Washington, DC (US)

(73) Assignee: Eypex Corporation, Pontiac, MI (US)

( * ) Notice: Subject to any disclaimer, the term of this patent is extended or adjusted under 35 U.S.C. 154(b) by 715 days.

(21) Appl. No.: 17/808,860

(22) Filed: Jun. 24, 2022

(65) Prior Publication Data

US 2022/0409756 A1      Dec. 29, 2022

Related U.S. Application Data

(60) Provisional application No. 63/215,380, filed on Jun. 25, 2021.

(51) Int. Cl.
*A61L 2/10* (2006.01)
*A61L 2/08* (2006.01)
*A61L 2/085* (2026.01)

(52) U.S. Cl.
CPC ................. *A61L 2/10* (2013.01); *A61L 2/085* (2013.01)

(58) Field of Classification Search
USPC .................................................... 250/455.11
See application file for complete search history.

(56) References Cited

U.S. PATENT DOCUMENTS

| | | | | |
|---|---|---|---|---|
| 2017/0296686 A1* | 10/2017 | Cole | .......................... | A61L 2/26 |
| 2018/0207302 A1* | 7/2018 | Vasilenko | ............... | A61L 2/238 |
| 2019/0083666 A1* | 3/2019 | Friberg | ................ | A61K 36/185 |
| 2020/0053856 A1* | 2/2020 | Barber | ................. | H05B 47/105 |

* cited by examiner

*Primary Examiner* — Kiet T Nguyen
(74) *Attorney, Agent, or Firm* — Butzel Long

(57) ABSTRACT

An electronic sanitizing device includes a germicidal light source and one or both of a red light source or a near infrared light source. The germicidal light source is configured to output germicidal light with a peak wavelength of 250 to 270 nanometers. The red light source is configured to output red light with a peak wavelength of 620 to 700 nanometers. The near infrared light source is configured to output near infrared light with a peak wavelength of 800 to 1200 nanometers.

20 Claims, 5 Drawing Sheets

600

100

| Controller 110 | Power Source 120 | Germicidal Light Source(s) 130 |
| --- | --- | --- |

140

| Red Light Source(s) 150 | Infrared Light Source(s) 160 | Comm. Device 190 |
| --- | --- | --- |

| User Sensor(s) 170 | Physical User Sensor(s) 170a | User ID Sensor(s) 170b |
| --- | --- | --- |

| Indicator Output(s) 180 | Visual Indicator 180a | Audio Indicator 180b |
| --- | --- | --- |

110

211    212    213    214

215

600

ELECTRONIC SANITIZING DEVICES AND METHODS

CROSS-REFERENCE TO RELATED APPLICATION(S)

This application claims priority to and the benefit of U.S. Provisional Application No. 63/215,380, filed Jun. 25, 2021, titled Electronic Sanitizing Device, the entire disclosure of which is incorporated by reference herein.

TECHNICAL FIELD

This disclosure relates to sanitizing and, in particular, electronic sanitizing devices for hands.

BACKGROUND

Bacteria, viruses, and other pathogens may be carried on hands and objects of people. Washing hands and disinfecting surfaces of objects with cleaning solutions (e.g., soap, bleach, etc.), however, is often performed inadequately or may be inconvenient.

SUMMARY

Disclosed herein are implementations of electronic sanitizing devices and methods related thereto.

In one implementation, an electronic sanitizing device includes a germicidal light source and one or both of a red light source or a near infrared light source. The germicidal light source is configured to output germicidal light with a peak wavelength of 250 to 270 nanometers. The red light source is configured to output red light with a peak wavelength of 620 to 700 nanometers. The near infrared light source is configured to output near infrared light with a peak wavelength of 800 to 1200 nanometers.

The electronic sanitizing device may include both the red light source and the near infrared light source. The red light may have a peak wavelength of 660 nanometers. The near infrared light may have a peak wavelength of 910 nanometers. Irradiance of the red light or the near infrared light may be greater than that of the germicidal light. The electronic sanitizing device may further include a controller configured to operate the germicidal light source and the one or both of the red light source or the near infrared light source according to a cleaning program by which energy density of one or both of the red light or the near infrared light is greater than the energy density of the germicidal light.

BRIEF DESCRIPTION OF THE DRAWINGS

The disclosure is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

DETAILED DESCRIPTION

An electronic sanitizing device outputs germicidal light for sanitizing users' skin, such as their hands, or coverings thereof (e.g., gloves). The electronic sanitizing device, being configured for sanitizing users' hands, may also be referred to as an electronic hand sanitizing device. The various embodiments of the electronic sanitizing device advantageously be used in environments in which people are required to repeatedly sanitize their hands, such as in medical care facilities and food service establishments. As used herein, the terms "sanitizing," "sanitize," or similar refer to killing or otherwise inactivating or destroying bacteria, viruses, or other pathogens, on surfaces of users' hands, skin, or objects and be considered to include disinfecting and/or sterilizing such surfaces. The electronic sanitizing device may also be referred to as a cleaning device, a light-based cleaning device, or an ultraviolet cleaning device.

Germicidal light is ultraviolet electromagnetic radiation having a suitable wavelength for killing or otherwise inactivating or destroying various bacteria, viruses, and other pathogens. In various embodiments, the electronic sanitizing device emits the germicidal light with a peak wavelength of 250 to 270 nanometers (e.g., 254 nanometers and/or 265 nanometers) in conjunction with red light and/or near infrared light at other peak wavelengths that may provide beneficial effects (e.g., to skin health) and/or may counter negative effects from the germicidal light. The term "peak wavelength" refers to a wavelength at which the magnitude of the light output by the electronic sanitizing device, or the various light sources thereof, is at a singular or local maxima.

Figures 1, 2:
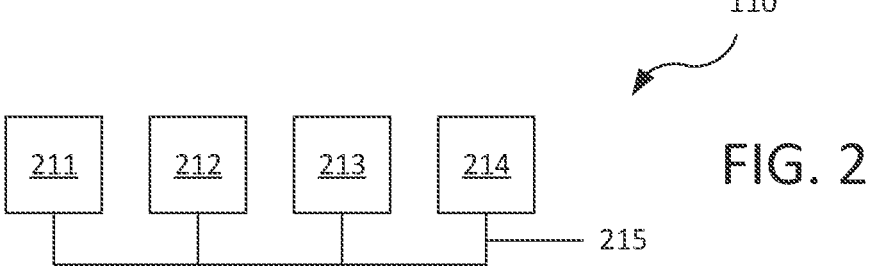
FIG. 1 is a schematic view of an electronic sanitizing device.
FIG. 2 is a schematic view of a controller of the electronic sanitizing device of FIG. 1.
Figures 3A, 3B:
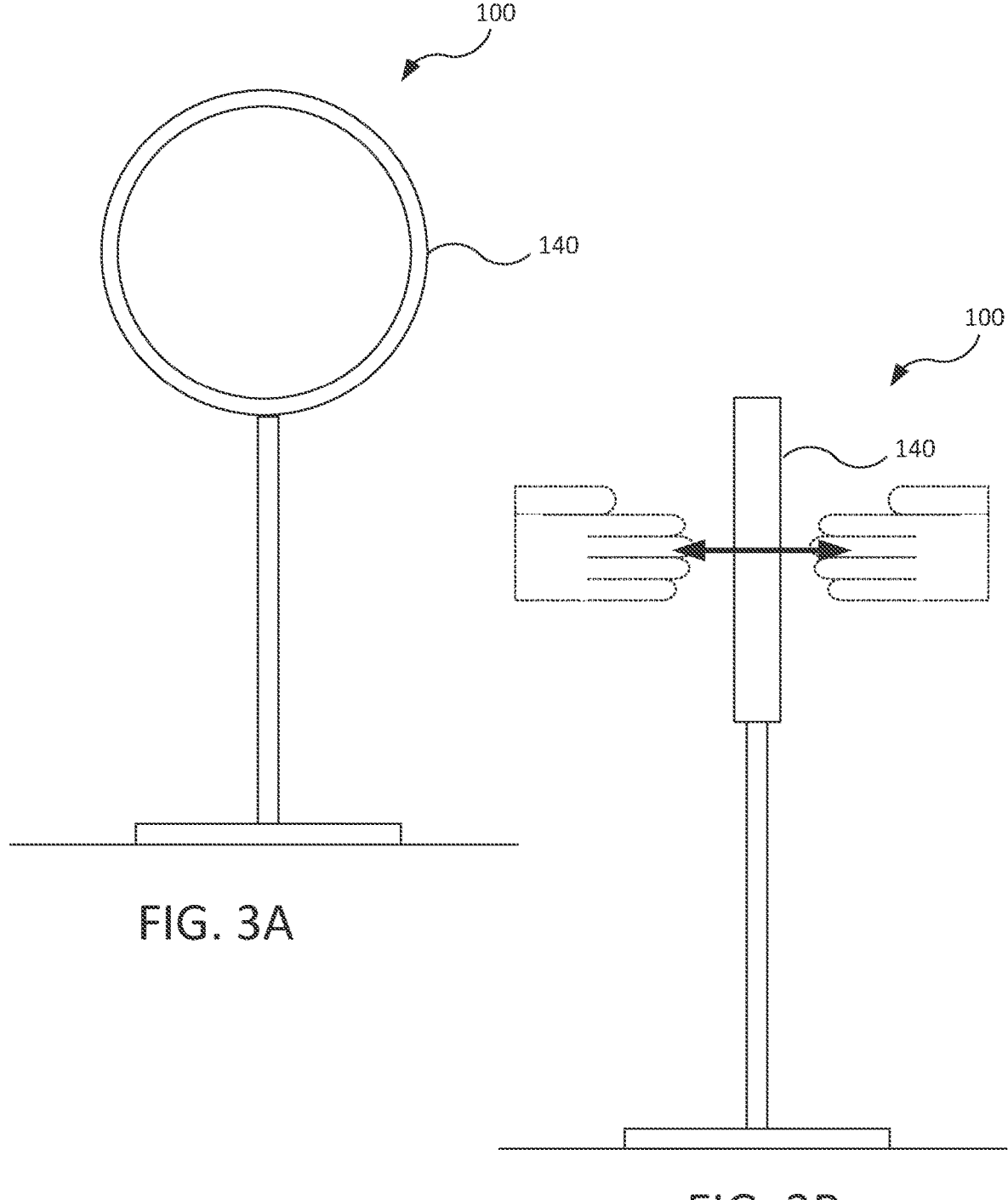
FIGS. 3A and 3B are front and side views of the electronic sanitizing device having a first embodiment of a chassis.
Figures 3C, 3D:
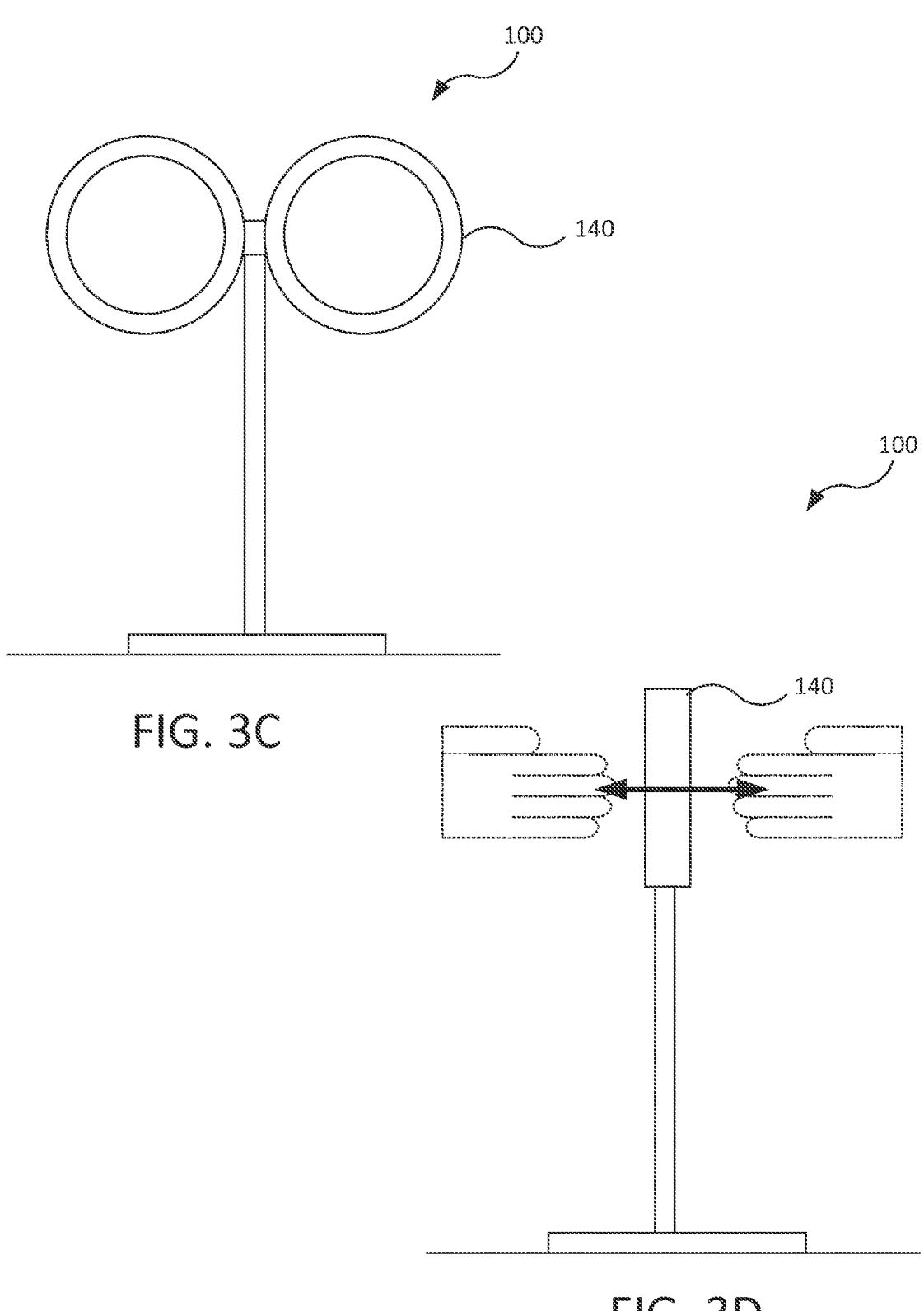
FIGS. 3C and 3D are front and sides views of the electronic sanitizing device having a second embodiment of a chassis.

Referring to FIG. 1, a schematic is shown of primary components of an electronic sanitizing device 100. The electronic sanitizing device 100 generally includes a controller 110, a power source 120, one or more germicidal light sources 130, and a chassis 140, along with one or more red light sources 150 and/or one or more infrared light sources 160. The one or more germicidal light sources 130, along with the one or more red light sources 150 and/or the near infrared light sources 160, may be referred to cooperatively as the polychromatic light sources 130, 150, 160. The polychromatic light sources 130, 150, 160 are coupled to and supported by the chassis 140, while the controller 110 operates the polychromatic light sources 130, 150, 160, for example, by controlling delivery of electrical power thereto from the power source 120 according to a cleaning program. The electronic sanitizing device 100 may further include one or more user sensors 170, one or more indicator outputs 180, and/or one or more communications devices 190, each of which may be coupled to the chassis 140 and operated by the controller 110, for example, by controlling delivery of electrical power thereto from the power source 120 and/or sending and/or receiving signals therebetween.

The controller 110, which may also be referred to as a processing apparatus, may be any suitable device or combination of devices suitable for operating the electronic sanitizing device 100 in the manners described herein. The controller 110 may, for example, be configured or otherwise provided as an application specific integrated circuit, programmable logic array, or other suitable hardware device or circuitry. Referring to FIG. 2, in one example, the controller 110 may have a hardware configuration that includes a processor 211, a storage 212, a memory 213, a communications interface 214, and a bus 215 connected therebetween. The processor 211 may be any suitable processor, such as a central processing unit, for executing computer instructions and performing operations described thereby. The storage 212 may be a non-volatile storage device, such as a hard-disk drive (HDD) or solid state storage device (SSD), which may be a computer readable medium that stored instructions (e.g., software code) that is executed by the processor 211 for operating the electronic sanitizing device 100 as described herein. The memory 213 may be a volatile, high-speed memory, such as random access memory (RAM). The communications interface 214 is in communication with other electronic components of the electronic sanitizing device 100 and enables communication therebetween. In another example, the controller 110 may be replaced with a manual switch that is operable by the user.

The power source 120 may be any suitable power source for receiving and/or storing electrical power for operating the various electronic components of the electronic sanitizing device 100, including the controller 110 and the poly-chromatic light sources 130, 150, 160, as well as any other included electronic components (e.g., the user sensors 170, the indicator outputs 180, and/or the communications device 190, among any other include electronic components). The power source 120 may be considered to include any circuitry or other components appropriate for conditioning the electrical power for use by the electronic components. In one example, the power source 120 may be or include a battery, such as removable battery pack. In the case of the power source 120 including a battery, the electronic sanitizing device 100 may further include a physical power connector (e.g., a wall plug, USB socket) or wireless connector (e.g., inductive charging coil) for connecting to and receiving electrical power from an external power source (e.g., a power source of a building, another battery), which may recharge the battery of the power source 120 and/or supply electrical power to the electronic components of the electronic sanitizing device 100. In another example, the power source 120 may be or include a conventional plug or hardwire connection for connecting to a continuous power source of a building (e.g., a wall outlet or electrical box that outputs alternating current (AC) electrical power).

Each of the germicidal light sources 130 emits germicidal light, which is ultraviolet electromagnetic radiation of a suitable wavelength for killing or otherwise inactivating or destroying various bacteria, viruses, or other pathogens. Cooperatively, the one or germicidal light sources 130 are configured to emit the germicidal light for killing or otherwise inactivating or destroying the various bacteria, viruses, and other pathogens, for example, on the surface to be cleaned (e.g., sanitized).

The germicidal light source 130 may emit the germicidal light at a peak wavelength of 250 nanometers to 270 nanometers (e.g., 254 nanometers or 265 nanometers), which is in the ultraviolet (UV) spectrum and, in particular, the UVC spectrum.

The one or more red light sources 150 and the one or more near infrared light sources 160 may be utilized to provide various health benefits to the users and may further offset and negative effects exposure to the germicidal light. While the germicidal light inactivates germs, the germicidal light may negatively impact human skin cells, for example, by increasing reactive oxygen species that may impact skin cell health and vitality and/or causing skin cells to undergo apoptosis. The red light and the near infrared light may provide benefits to the skin that counter and/or may provide net positive benefits to skin health. The health benefits from the red light and/or near infrared light may be time-delayed (e.g., fractions of a second, seconds, minutes, hours) and/or be cumulative in nature, such that benefits may be expected for heavy repeat users of the sanitizing device (e.g., one or more times per day).

For example, red light is believed to provide improved cell growth, collagen production, microcirculation, DNA repair, antioxidation, and anti-apoptosis benefits. Red light is also believed to contribute to increased production of adenosine triphosphate (ATP) by dissociating nitric oxide from bound respiration enzyme. Red light is still further believed to result in reduced apoptosis through increased cell proliferation and/or suppression of apoptosis. As further examples, near infrared light is believed to prepare cells to resist stress related to UV exposure. Near infrared light is believed to promote proliferation of cells and increase gene expression of anti-inflammatory cytokines and suppression of pro-inflammatory mediators. Near infrared light is also believed to stimulate protein and collagen growth that provide UV protection. Thus, by providing red light and/or near infrared light in conjunction with the germicidal light, health benefits may be achieved and/or negative effects of the germicidal light countered.

The one or more red light sources 150 are configured to emit light at a peak wavelength of 620 to 700 nanometers (e.g., 660 nanometers). The one or more near infrared light sources 160 are configured to emit light at a peak wavelength of 800 to 1200 nanometers (e.g., 910 nanometers).

Each of the polychromatic light sources 130, 150, 160 may be or include one or more light emitting diodes (LED) that emit the germicidal light, the red light, or the near infrared light, respectively, or any other suitable light output device or devices (e.g., incandescent, excimer, or gas-discharge bulbs or lamps). The polychromatic light sources 130, 150, 160 are configured to output the light onto a common surface that is to be cleaned (e.g., sanitized), such as that of a hand or other object of a user.

The polychromatic light sources 130, 150, 160 may be configured and operated in various different manners to provide sanitizing effects from the germicidal light sources 130 and health benefits from the red light sources 150 and the near infrared light sources 160. The sanitizing device 100 is configured to be operated by a controller according to a cleaning program to output sufficient light from the poly-chromatic light sources 130, 150, 160 to achieve desired results. The cleaning program includes a predetermined set of instructions according to which the controller 110 operates the polychromatic light sources 130, 150, 160, for example, by providing predetermined amounts of electrical current thereto over predetermined amounts of time.

The total output from the polychromatic light sources 130, 150, 160 during the cleaning program may be referred to as energy density or a dose and may be measured as energy per surface area (i.e., $J/cm^2$). The energy density may be measured at the surface to be sanitized (e.g., of a hand of a user or expected location of the hand). The sanitizing device 100 may be configured, for example, with the controller 110 operating the polychromatic light sources 130, 150, 160 according to the cleaning program to output higher energy density of the near infrared light than the germicidal light and/or higher energy density of the red light than the near infrared light and/or the germicidal light.

Without being limited to a particular theory, it is believed that having higher energy density of the red light and/or the near infrared light than the germicidal light may be beneficial due to higher penetration depths of the near infrared light and the red infrared light than the germicidal light into the skin of users.

The cleaning program may be configured to provide energy density of approximately 5 to 30 mJ/cm^2 of the germicidal light (e.g., approximately 15 to 25 mJ/cm^2, such as approximately 20 mJ/cm^2), approximately 50 to 500 mJ/cm^2 of the near infrared light (e.g., approximately 100 to 300 mJ/cm^2, such as approximately 200 mJ/cm^2), and approximately 200 to 2000 mJ/cm^2 of the red light (e.g., approximately 500 to 1250 mJ/cm^2, such as approximately 700 to 1000 mJ/cm^2). The energy density may, instead or additionally, be defined in relative terms, such as the energy density of the near infrared light being 2 to 20 times that of the germicidal light (e.g., 5 to 15 times, such as approximately 10 times) and/or the energy density of the red light being 5 to 100 times that of the germicidal light (e.g., 20 to 80 times, such as 40 to 60 times). Alternatively, the sanitizing device 100 may be configured to output the germicidal light with the same or higher energy density than the red light and/or near infrared light.

To achieve energy density, the light is output during the cleaning program with irradiance (i.e., W/cm^2, which may also be referred to as power or power density) over time. The irradiance may be measured at the surface to be sanitized (e.g., of a hand of a user or expected location of the hand). The irradiance may, for example, be 2 to 10 mW/cm^2 for the germicidal light (e.g., 3 to 8 mW/cm^2, such as approximately 4 to 5 mW/cm^2), 25 to 150 mW/cm^2 of the near infrared light (e.g., 60 to 100 mW/cm^2), and/or 50 to 400 mW/cm^2 of the red light (e.g., 100 to 300 mW/cm^2). The irradiance of the polychromatic light sources 130, 150, 160 may also be defined in relative terms, for example, with irradiance of the near infrared light being greater than five times that of the germicidal light (e.g., 5 to 30 times, such as 10 to 20 times) and/or the irradiance of the red light is greater than ten times that of the germicidal light (e.g., 10 to 100 times that of the germicidal light, such as 20 and 50 times). Alternatively, the sanitizing device 100 may be configured to output the germicidal light with the same or higher irradiance than the red light and/or near infrared light.

The germicidal light, the near infrared light, and/or the red light may be output by the polychromatic light sources 130, 150, 160 at various times and/or with various durations according to the cleaning program. For example, the germicidal light, the near infrared light, and/or the red light may be output at the same time for the same duration, for example, starting, stopping, and operating simultaneously over a total duration of the cleaning program of 1 to 20 seconds (e.g., 3 to 10 seconds, such as approximately 5 seconds). As such, the germicidal light may be output concurrently with the red light and/or near infrared light. Alternatively, the near infrared light and/or the red light may start before the germicidal light (e.g., 0.1 to 1 second, such as ¼ to ½ of a second). It is theorized that providing the near infrared light and/or the red light may activate various skin cells (e.g., genes thereof) to prepare the skin cells for subsequent receipt of the germicidal light thereon (e.g., for protection therefrom). The near infrared and/or the red light may also stop at different times (e.g., after) the germicidal light (e.g., 0.1 to 10 seconds thereafter), for example, to provide the desired energy density from the polychromatic light sources 130, 150, 160. Alternatively, the sanitizing device 100 may be configured to output the germicidal light with the same or longer duration than the red light and/or near infrared light. In still further examples, the germicidal light may be output at a different time than the red light and/or near infrared light, for example, after or between output of the red light and/or near infrared light.

The sanitizing device 100 may begin operating the polychromatic light sources 130, 150, 160 according to the cleaning program, for example, upon detection of the hand or other object of the user with the user sensor 170 and/or upon other input from the user (e.g., pressing a button or otherwise providing a signal to the sanitizing device 100 to begin cleaning program).

Figure 4:
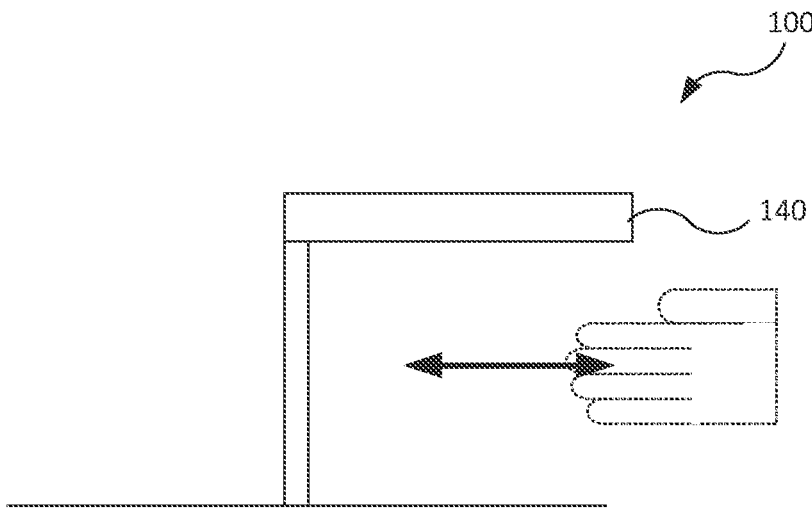
FIG. 4 is a side view of the electronic sanitizing device having a third embodiment of a chassis.
Figure 5:
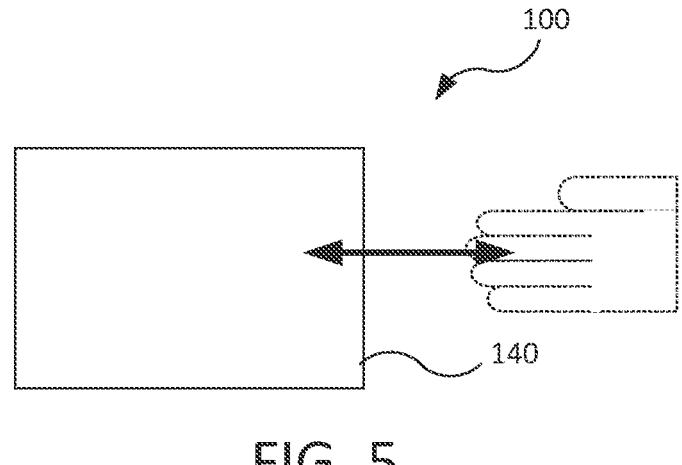
FIG. 5 is a side view of the electronic sanitizing device having a fourth embodiment of a chassis.

The chassis 140 is a structure that is coupled to and supports the polychromatic light sources 130, 150, 160. As discussed in further detail below, the chassis 140 is cooperatively configured with the polychromatic light sources 130, 150, 160 to emit the germicidal light to sanitize users' hands or object and may also prevent or hinder undesirable human exposure to the germicidal light. For example, as shown in FIG. 3A-3D, the chassis 140 may be configured with one ring (see FIGS. 3A-3B) or multiple rings (see FIGS. 3C-3D) to which the polychromatic light sources 130, 150, 160 are coupled to and configured to emit light inwardly and across an opening of the ring. As the user inserts their hands through the opening of the ring, the polychromatic light sources 130, 150, 160 emit the germicidal light and/or the red light and/or the near infrared light onto the user's hands. In another example shown in FIG. 4, the chassis 140 may configured as a suspended surface to which the polychromatic light sources 130, 150, 160 are coupled to and configured to emit light downwardly therefrom. As the user inserts their hands under the surface, the polychromatic light sources 130, 150, 160 emit the germicidal light and/or the red light and/or the near infrared light onto the user's hands. As shown in FIG. 5, the chassis 140 may be configured as a compartment in which the polychromatic light sources 130, 150, 160 are positioned and configured to emit and/or reflect light therein. As the user inserts their hands into the compartment, the polychromatic light sources 130, 150, 160 emit the germicidal light and/or the red light and/or the near infrared light onto the users' hands directly and/or reflectively.

The one or more user sensors 170 are configured to detect the user, for example, detecting hands of the user being physically in or near the sanitizing region and/or identifying the user. For example, the one or more user sensors 170 may include one or more physical sensors 170a that are configured to detect one or more hands of the user within or in proximity to the electronic sanitizing device 100. Upon detection with the physical sensors 170a, the controller 110 may operate the germicidal light source 130, as well as the visible light source 150 and the near infrared light source 160 if included. The physical sensor 170a may be any suitable type of sensor using any suitable type of sensing, such as being laser-based (e.g., a laser range finder), light-based (e.g., any light-based sensor with or without a light emitter, such as a passive infrared sensor, infrared sensor with infrared emitter, ambient light sensor), image-based (e.g., video image recognition), or acoustic-based (e.g., ultrasonic or radar sensors).

The one or more user sensors 170 may also include an identification sensor 170b that is used to determine the identity of the user. The identification sensor 170b may, for example, be a communications device that communicates with another device associated with the user (e.g., a phone, other electronic device, or key card using radio-frequency identification (RFID), near field communication (NFC), Bluetooth, Wi-Fi, or other suitable communications protocol), an optical or magnetic scanner that scans personal identification of the user (e.g., bar code or magnetic strip associated with a driver license or other form of personal identification), or a camera or other optical device (e.g., using facial recognition). In the case of the identification sensor 170*b*, the identity of the user may be used to enable (e.g., provide permission) the electronic sanitizing device 100 to be used by the user and/or may track usage of the electronic sanitizing device 100 by each such user. Tracking usage of the electronic sanitizing device 100 by user may be advantageous for monitoring workers, for example, for compliance with safety and/or cleanliness policies and protocols in different workplaces (e.g., hospitals and other health care facilities, restaurants and other hospitality environments). User usage information may be stored in memory (e.g., of the controller 110) and transmitted to a computing device (e.g., with the communications device 190) that may store usage information. User usage information may, for example, include a user identifier (e.g., name or user number), time stamp (e.g., the time at which a sanitizing device 100 is used by the user), and/or a device identifier (e.g., uniquely identifying the particular sanitizing device 100 among multiple of the sanitizing devices 100).

The one or more indicator outputs 180 are configured to provide audio and/or visual outputs pertaining to the electronic sanitizing device 100, such as instructions, starting, and/or stopping operation of the sanitizing device 100. The one or more indicator outputs 180 may, for example, include one or more visual indicators 180*a* and/or one or more audio indicators 180*b*.

The communications device 190 is configured to communicate with computing devices external to the sanitizing device 100. In one example, as described previously, the communications device 190 may send data containing usage information to another computing device for tracking usage of one or more of the sanitizing devices 100 by one or more users. In other examples, the communications device 190 may send data communicating other information, such as the operational status of the sanitizing device 100 or aggregated usage statistics (e.g., uses per unit time or particular times). The communications device 190 may be any suitable communications device capable of communicating via any suitable communications protocol, such as cellular, Wi-Fi, or Bluetooth.

Figure 6:
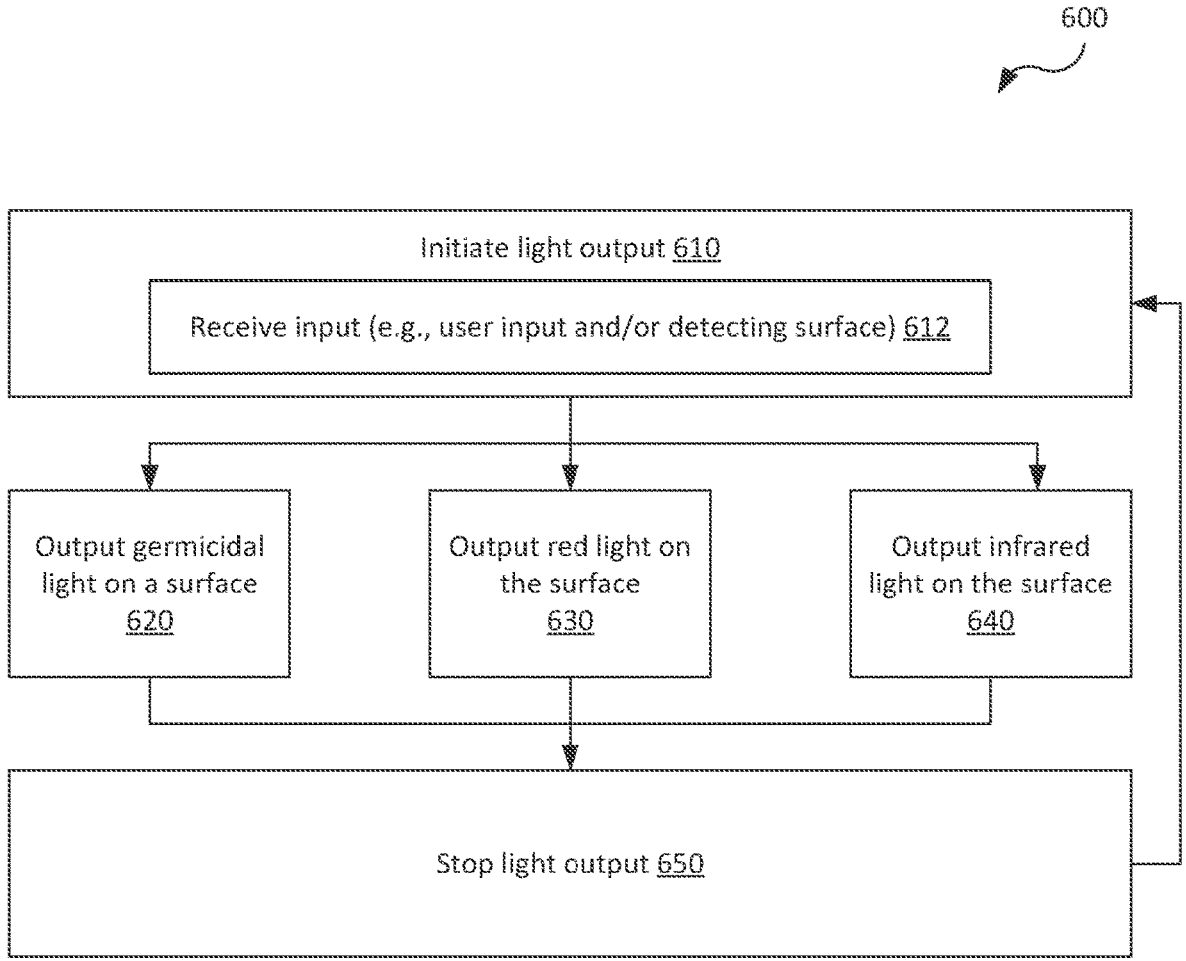
FIG. 6 is a flowchart of a method for sanitizing a surface with the electronic sanitizing device of FIG. 1.

Referring to FIG. 6 a method 600 is provided, such as a method for outputting germicidal light or a cleaning method. The method 600 generally includes outputting 620 germicidal light and one of both of outputting 630 red light and/or outputting 640 infrared light. The method 600 may further include initiating light output 610 and stopping light output 650.

The outputting 620 of the germicidal light is performed with one or more germicidal light sources, which may be of a sanitizing device, such as the one or more germicidal light sources 130 of the sanitizing device 100, as described previously. The outputting 620 includes outputting the germicidal light onto a surface to be cleaned, which may be the skin of a person (e.g., a hand of a user) and/or object (e.g., such as an electronic device, utensil, instrument, or other object of a user).

The outputting 630 of the red light is performed with one or more red light sources, which may be of a sanitizing device, such as the one or more red light sources 150 of the sanitizing device 100, as described previously. The outputting 630 includes outputting the red light onto the surface to be cleaned. The outputting 630 may include outputting the red light with a lower, same, or greater energy density, irradiance, and/or time as that of the outputting 620 of the germicidal light, as described previously. The outputting 630 of the red light may be performed concurrent with the outputting 620 of the germicidal light. The outputting 630 of the red light may begin prior to, simultaneous with, or after the outputting 620 of the germicidal light, as described previously. The outputting 630 of the red light may stop prior to, simultaneous with, or after the outputting 620 of the germicidal light, as described previously.

The outputting 640 of the near infrared light is performed with one or more infrared light sources, which may be of a sanitizing device, such as the one or more infrared light sources 160 of the sanitizing device 100, as described previously. The outputting 640 includes outputting the near infrared light onto the surface to be cleaned. The outputting 640 may include outputting the near infrared light with a lower, same, or greater energy density, irradiance, and/or time as that of the outputting 620 of the germicidal light, as described previously. The outputting 640 of the near infrared light may be performed concurrent with the outputting 620 of the germicidal light and/or the outputting 630 of the red light. The outputting 640 of the near infrared light may begin prior to, simultaneous with, or after the outputting 620 of the germicidal light, as described previously. The outputting 640 of the near infrared light may stop prior to, simultaneous with, or after the outputting 620 of the germicidal light, as described previously.

The initiating 610 of the light output includes beginning 614 the outputting 620, 630, and/or 640. For example, a controller, such as the controller 110 of the electronic sanitizing device 100, may begin to operate the polychromatic light sources 130, 150, 160 according to predetermined instructions of a cleaning program. As described for each of the outputting 620, 630, 640, the germicidal light, the red light, and the near infrared light may begin to be output at different times.

The initiating 610 may further include receiving 612 an input, for example, to begin the outputting 620, 630, and/or 640. The input, may, for example, include receiving an input instruction (e.g., a button press or other signal) from a user and/or detecting the surface to be cleaned (e.g., a user and/or object), such as with the user sensors 170*a*. For example, the initiating 610 of the light output may be performed by the controller upon receiving one or more input signals thereto.

The stopping 650 of the light output includes stopping the outputting 620, 630, and/or 640. For example, the controller may stop operating the polychromatic light sources 130, 150, 160 according to the predetermined instructions of the cleaning program. As described for each of the outputting 620, 630, 640, the germicidal light, the red light, and the near infrared light may stop being output at different times.

The method 600 may be repeated for cleaning (e.g., sanitizing) additional surfaces (e.g., upon receiving 612 of another input).

While the disclosure has been described in connection with certain embodiments, it is to be understood that the disclosure is not to be limited to the disclosed embodiments but, on the contrary, is intended to cover various modifications and equivalent arrangements included within the scope of the appended claims, which scope is to be accorded the broadest interpretation so as to encompass all such modifications and equivalent structures as is permitted under the law.

What is claimed is:

1. An electronic sanitizing device comprising:

a germicidal light source configured to output germicidal light with a peak wavelength of 250 to 270 nanometers; and one or both of a red light source or a near infrared light source, the red light source being configured to output red light with a peak wavelength of 620 to 700 nanometers, and the near infrared light source being configured to output near infrared light with a peak wavelength of 800 to 1200 nanometers;

wherein irradiance of the red light or the near infrared light is greater than that of the germicidal light.

2. The electronic sanitizing device according to claim 1, comprising both the red light source and the near infrared light source.

3. The electronic sanitizing device according to claim 2, wherein the peak wavelength of the red light is 660 nanometers and the peak wavelength of the near infrared light is 910 nanometers.

4. The electronic sanitizing device according to claim 1, wherein the irradiance of the germicidal light is 2 to 10 mW/cm^2.

5. The electronic sanitizing device according to claim 1, further comprising a controller configured to operate the germicidal light source and the one or both of the red light source or the near infrared light source according to a cleaning program by which energy density of one or both of the red light or the near infrared light is greater than the energy density of the germicidal light.

6. The electronic sanitizing device according to claim 5, comprising the red light source, wherein the energy density of the red light is at least ten times that of the germicidal light.

7. The electronic sanitizing device according to claim 5, comprising the near infrared light source, wherein the energy density of the near infrared light is at least five times that of the germicidal light.

8. The electronic sanitizing device according to claim 5, wherein the energy density of the germicidal light is 5 to 30 mJ/cm^2.

9. The electronic sanitizing device according to claim 1, further comprising a chassis to which the germicidal light source and the one or both of the near infrared light source or the red light source are coupled and configured to emit the germicidal light and the one of both of the near infrared light or the red light onto a surface of a hand or an object in or under the chassis.

10. The electronic sanitizing device according to claim 1, comprising both the red light source and the near infrared light source, and further comprising a controller, and a chassis to which the germicidal light source and the one or both of the near infrared light source or the red light source are coupled and configured to emit the germicidal light and the one of both of the near infrared light or the red light onto a surface of a hand or an object in or under the chassis;

wherein the controller configured to operate the germicidal light source, the red light source, and the near infrared light source according to a cleaning program by which irradiance of the red light and the near infrared light are greater than that of the germicidal light, irradiance of the germicidal light is greater than 2 mW/cm^2, energy density of the red light and the near infrared light are greater than that of the germicidal light, and energy density of the germicidal light is greater than 5 to 30 mJ/cm^2.

11. The electronic sanitizing device according to claim 1, wherein each of the germicidal light source and the one or both of the red light source and the near infrared light source includes one or more light emitting diodes (LED) and/or one or more lamps.

12. An electronic cleaning device comprising:

a germicidal light source configured to output germicidal light having a peak wavelength of between 250 and 270 nanometers onto a surface to be cleaned;

a red light source configured to output red light onto the surface;

an infrared light source configured to output infrared light onto the surface;

a controller configured to operate the germicidal light source, the red light source, and the infrared light source according to predetermined instructions of a cleaning program with the germicidal light having a lower energy density on the surface than each of the red light and the infrared light.

13. A method for sanitizing a surface comprising:

outputting germicidal light with a germicidal light source and one or more of red light with a red light source or near infrared light with a near infrared light source onto a surface;

wherein the germicidal light has a first peak wavelength of 250 to 270 nanometers, the red light has a peak wavelength of 620 to 700 nanometers, and the near infrared light has a peak wavelength of 800 to 1200 nanometers; and wherein the outputting comprises one or more of the following:

outputting the germicidal light with a lower energy density than the one or more of the red light or the near infrared light; and beginning to output the germicidal light after beginning to output the one or more of the red light or the near infrared light.

14. The method according to claim 13, wherein the outputting includes outputting the red light with the red light source and the near infrared light with the near infrared light source onto the surface.

15. The method according to claim 13, wherein the outputting includes outputting the germicidal light concurrent with the one or more of the red light or the near infrared light.

16. The method according to claim 13, wherein the outputting includes outputting the germicidal light with a lower energy density than that of the one or more of the red light or the near infrared light;

wherein the outputting includes beginning to output the germicidal light after beginning to output the one or more of the red light or the near infrared light; and wherein the outputting includes outputting the germicidal light concurrent with the one or more of the red light or the near infrared light.

17. An electronic sanitizing device comprising:

a germicidal light source configured to output germicidal light with a peak wavelength of 250 to 270 nanometers; and one or both of a red light source or a near infrared light source, the red light source being configured to output red light with a peak wavelength of 620 to 700 nanometers, and the near infrared light source being configured to output near infrared light with a peak wavelength of 800 to 1200 nanometers;

wherein the irradiance of the germicidal light is 2 to 10 mW/cm$^2$.

18. The electronic sanitizing device according to claim 17, comprising both the red light source and the near infrared light source.

19. The electronic sanitizing device according to claim 18, wherein the peak wavelength of the red light is 660 nanometers and the peak wavelength of the near infrared light is 910 nanometers.

20. The electronic sanitizing device according claim 17, wherein each of the germicidal light source and the one or both of the red light source and the near infrared light source includes one or more light emitting diodes (LED) and/or one or more lamps.

* * * * *